United States Patent [19]
Tinker et al.

[11] Patent Number: 6,130,096
[45] Date of Patent: Oct. 10, 2000

[54] CHEMICAL COMPLEXES

[75] Inventors: Nigel Dennis Tinker, Preston; James Fraser Stoddart, Birmingham; Sayeedha Iqbal, Birmingham; Owen Allen Matthews, Birmingham, all of United Kingdom

[73] Assignee: British Nuclear Fuels PLC, Cheshire, United Kingdom

[21] Appl. No.: 08/973,228

[22] PCT Filed: Jun. 6, 1996

[86] PCT No.: PCT/GB96/01342

§ 371 Date: Mar. 20, 1998

§ 102(e) Date: Mar. 20, 1998

[87] PCT Pub. No.: WO96/39402

PCT Pub. Date: Dec. 12, 1996

[30] Foreign Application Priority Data

Jun. 6, 1995 [GB] United Kingdom .................. 9511396

[51] Int. Cl.$^7$ ...................... C07D 323/00; C07D 409/14; C08L 71/02
[52] U.S. Cl. .......................... 436/164; 549/352; 549/353; 525/187; 522/80.07; 522/82.08; 436/74; 436/79
[58] Field of Search ................................ 436/74, 79, 164; 549/352, 353; 525/187; 522/82.08, 80.07

[56] References Cited

U.S. PATENT DOCUMENTS

| | | | |
|---|---|---|---|
| 4,512,939 | 4/1985 | Dorr et al. | 264/0.5 |
| 4,554,362 | 11/1985 | Shono et al. | 549/352 |
| 4,734,376 | 3/1988 | Pacey et al. | 436/79 |
| 5,538,655 | 7/1996 | Fauteux et al. | 252/62.2 |

FOREIGN PATENT DOCUMENTS

| | | |
|---|---|---|
| 0 097 690 A2 | 6/1983 | European Pat. Off. . |
| 0 136 655 A2 | 9/1984 | European Pat. Off. . |
| 0 277 708 B1 | 10/1994 | European Pat. Off. . |
| 61-254887 | 11/1986 | Japan . |
| 62-225993 | 10/1987 | Japan . |
| 64-83188 | 3/1989 | Japan . |
| 2-67991 | 3/1990 | Japan . |
| 1 461 263 | 1/1976 | United Kingdom . |
| 2 156 144 | 4/1988 | United Kingdom . |

OTHER PUBLICATIONS

"Transition Metal Templated FFormulation of [2]– and [3]–Rotaxanes with Porphyrins as Stopper" Chambron et al. J. Am. Chem. Soc. 1993 (115), 12378–12384 (1993) no month.

"A Chemically and electrochemically switchable molecular shuttle" Bissell et al, Nature 369/12, pp 133–137, May 1994.

Abstract of conferenced entitled Nuclear Design Method of GD–Loaded–MOX–Fueled Demonstration ART, presented at International Conference on Design and Safety of Advanced Nuclear Power Plants, Toyko, Japan, Oct. 25–29, 1992, published in Atomic Energy Society, Japan, 1992.

(List continued on next page.)

*Primary Examiner*—Jill Warden
*Assistant Examiner*—John C. Kim
*Attorney, Agent, or Firm*—Workman, Nydegger & Seeley

[57] ABSTRACT

Rotaxanes and pseudorotaxanes, methods of making them, intermediates in their formation and methods of using them in sensors are provided based upon changes in color absorption upon cation contact.

17 Claims, 6 Drawing Sheets

OTHER PUBLICATIONS

Abstract of Japanese Patent Applicatnion No. JP4265896, dated Sep. 22, 1993, class 3, subclass 62, entitled Nuclear Fuel Assemble Lgith Water Reactor Contain Uranium Plutonium Fission Material Rod Combust Poison.

Abstract of Japanese Patent Application No. JP 55006267, dated Jan. 17, 1980, class 3 subclass 62, entitled Nuclear Fuel Produce Powder Comprise Uranium Di Oxide Plutonium Dioxide Mixture One Compound Gadolinium Dioxide.

Abstract of Japanese Patent Application No. JP 3137596, dated Jun. 12, 1991, class 3, subclass 62, entitled Nuclear Fuel Pellet Improve Fission Product Gas Retentivity Inner Part Uranium Plutonium Dioxide Outer Part Material Contain Gadolinium Oxide.

Abstract of Japanese Patent Application No. 63293489, dated Nov. 30, 1988, class 3, subclass 30, entitled Nuclear Fuel Assemble Comprise Uranium Fuel Rod Mix Oxide Fuel Rod.

Benniston, Andrew C., Harriman, Anthony, and Lynch, Vincent M., "Photoactive [2] Rotaxanes Formed by Multiple π–Stacking", *Tetrahedron Letter*, vol. 35, No. 10, 1994, pp. 1473–1476.

Aneilli, Pier Lucio, Ashton, Peter R., Ballardini, Roberto, Balzani, Vincenzo, Delgado, Milagros, Gandolfi, Maria Teresa, Goodnow, Timothy T., Kaifer, Angel E., Philp, Douglas, Pietraszkiewicz, Marek, Prodi, Luca, Reddington, Mark V., Slawin, Alexandra M. Z., Spencer, Neil, Stoddard, J. Fraser, Vicent, Cristine, and Williams, David J., "Moledular Meccano. 1. [2] Rotaxanes and a [2] Catenance Made to Order", *American Chemical Society*, 1992, vol. 114, pp. 193–218.

"Heterocycllic Compounds (More Than One Hetero Atom)", *Chemical Abstracts*, 1996, vol. 124, No. 21, p. 1341.

Stoddart, Philp D., "Self–Assembly in Organic–Synthesis", *Synlett*, 1991, N7, pp. 445–458 (abstract).

Examples of X or Y =

|||| = π-π stacking

CHEMICAL COMPLEXES

The present invention relates to chemical complexes in particular rotaxanes and pseudorotaxanes formed by addition of cationic cyclophanes and acyclic polyether derivatives, polyether derivatives useful in the preparation of such rotaxanes and pseudorotaxanes, uses of such rotaxanes and pseudorotaxanes and devices incorporating such rotaxanes and pseudorotaxanes.

There has been considerable recent interest concerning the control of molecular architectures in both the solid state and in solution. The known processes of molecular recognition and self-assembly have been employed to generate a number of topologically interesting and functioning supramolecular entities. One such known complex, a [2]pseudorotaxane (illustrated herein) is formed by interaction of two components, viz., an acyclic polyether derivative containing a π-electron rich unit and an encircling π-electron deficient cyclophane unit.

The purpose of the present invention is to provide by interaction of a cyclophane and an acyclic polyether derivative a novel rotaxane or pseudorotaxane complex which has unexpected novel and useful properties. Where reference is made hereafter to rotaxanes, including the claims, it should be taken to include reference to pseudorotaxanes also.

According to the present invention in a first aspect there is provided a rotaxane complex which is formed by interaction between an acyclic polyether derivative containing one or more π-electron rich units and an encircling π-electron deficient cyclophane unit, the acyclic polyether chain having terminal units inhibiting slippage of the cyclophane from the thread, at least one of the terminal units comprising a cation receptor unit.

The rotaxane complex of the first aspect is therefore formed by π—π interaction between two compounds, Components 1 and 2, described as follows.

Component 1 is an acyclic polyether derivative containing one or more than one π electron rich functional units. Preferably component 1 has at least two different π electron rich functional units. The π electron rich units may or may not be aromatic. Examples include 1,4 dioxybenzene, 1,5 dioxynaphthalene, tetrathiafulvalene groups.

The acyclic polyether thread of Component 1 may be of the same length or of different lengths at either side of the π electron rich units.

Component 1 may be of the structure provided in FIG. 1 wherein $R^1$ and $R^2$ are neutral terminal units at least one of which includes a cation receptor site, e.g., a crown ether unit; n is zero or a positive integer, m is independently zero or a positive integer and p is independently zero or a positive integer; X and Y each represent a covalent bond or a π-electron-rich functional unit but where X may or may not be the same as Y, and at least one of X and Y is an π-electron-rich functional unit. Preferably x and y are different.

The thread has terminal units which may inhibit slippage of the cyclophane from the chain. Such terminal stopper units may allow or slightly inhibit dissociation of Components 1 and 2 where they are relatively small (pseudorotaxanes) or may prevent dissociation under most normal conditions where they are larger units (rotaxanes). At least one of the terminal units is preferably a neutral cation receptor unit. Examples of suitable neutral, cation-binding terminal units are macrocyclic polyethers such as crown-ethers, azacrown ethers, thiocrown ethers cyclams, porphyrins, calixanes, calixacrowns and calixaspherands. Examples of non-cation binding terminal units are: $SiR_3$, $SiPh_3$, (where R may be alkyl, arylalkyl etc. Ph is phenyl etc.), OH, OR (R=alkyl), SH, $NH_2$.

The terminal unit may be of crown form according to the formula a-crown-b where a is the number of atoms in the cyclic unit and b is the number of hetero atoms in the ring, with a varying between 8 and 45, preferably 8 and 24 and b varying between 3 and 25, preferably 3 and 10.

The crown ether may be specific for one or more types of particular cations. For instance 12-crown 4 is lithium ion specific.

Component 2 is a π electron deficient cyclophane. A cyclophane is a large ring compound incorporating aromatic units in the ring, one or more of the aromatic units being a π-electron deficient aromatic unit.

The cyclophane unit exists as a cationic compound and is associated with anion(s) to counterbalance the charge(s), for instance in tetracationic form. A variety of anions (e.g., halides) may be employed in the cyclophane, although $PF_6$ ions are preferred because of the enhanced solubilities they provide in organic solvents. Solubilities in different solvents can be controlled by careful choice of anions.

The said rotaxane is usually formed in a liquid medium, but may exist in either the solid state or in solution.

According to the present invention in a second aspect there is provided a cation complexed to a rotaxane as defined in the first aspect at the cation receptor site of at least one of its said terminal units.

According to the present invention in a third aspect there is provided a method of detecting a cation in a medium in contact with the rotaxane which comprises detecting changes in the intensity and/or wavelength of the absorption spectrum of the rotaxane.

In the method of the third aspect the rotaxane molecules are desirably aggregated and supported. For example, they may be deployed as a discrete region, e.g., formed by screen printing, in a thin film supported on a suitable substrate of glass or polymeric material. Alternatively, they may be formed as a film attached to, for instance, a polymer or siliceous surface. Furthermore, a thin film sensor element incorporating the rotaxane molecules may be incorporated into a photodetection system using either an optical waveguide and photodetector or photodetectors or low noise charge coupled devices (CCDs).

The method of detection according to the third aspect may comprise detecting a change in the absorption intensity at a given wavelength or a change in the ratio of absorption intensities at two different wavelengths. Detection of the said change may be carried out in one of the ways well known to those skilled in the photodetection art, e.g., by observing changes in the radiation reflected or transmitted after absorption using a spectrophotometer or a photodetector optionally with a color filter.

The cation to be detected may comprise any metal ion, e.g., $Cs^+$ or non-metal cation, e.g., an ammonium or alkylammonium ion or zwitterionic species. The presence or a measure of the concentration of cations may be detected by measuring changes in the absorption spectrum of the rotaxane according to the first aspect.

The method according to the third aspect is useful in a variety of applications. Solutions containing cations to be detected by the method according to the third aspect may for example be produced in the following ways:

(i) the decontamination of surfaces contaminated with radioactive, toxic or other metal species, e.g., using as a decontamination agent an inorganic acid such as nitric, sulphuric or fluoroboric acid or an organic acid such as citric or formic acid;

(ii) as aqueous liquids produced in chemical streams;

(iii) as effluent streams produced by chemical processing operations;

(iv) as biological samples such as blood, serum etc.

In all of these applications samples may be produced which, with various known degrees of pre-treatment, may be converted into aqueous test samples for metal ion sensing or analysis by the method according to the fourth aspect.

The cation to be detected may comprise for example an alkali metal ion. The presence or concentration of radioactive caesium, for example, may advantageously be detected using the absorption spectrum of the rotaxane of the first aspect of the present invention in the method of the third aspect.

The method according to the third aspect of the present invention therefore provides a particularly convenient way of detecting cations present as trace components in a test solution.

According to the present invention in a fourth aspect there is provided an acyclic polyether derivative which comprises Component 1 as specified hereinbefore.

The polyether derivative of the fourth aspect may for example be prepared from an equivalent precursor molecule having terminal hydroxyl groups. This diol may be treated to afford its corresponding bistosylate e.g., by use of tosyl chloride. The bistosylate may be reacted with the appropriate crown ether molecules, e.g., using sodium hydride in a suitable solvent such as tetrahydrofuran.

According to a fifth aspect of the invention we provide a device for detecting the presence of one or more cations in a medium, the device comprising a sensor provided with one or more rotaxanes or pseudorotaxanes according to the first aspect of the invention and means for monitoring the light absorption characteristics of the sensor.

The device may provide a qualitative or quantitative reading. The device may be specific to certain classes of cations, such as a particular group of the periodic table, or be specific to an individual cation for instance caesium.

Embodiments of the present invention will now be described by way of example with reference to the accompanying drawings, in which:

FIG. 1 illustrates the structure of an acyclic polyether useful in the formation of rotaxanes and pseudorotaxanes;

FIGS. 2a–b illustrate a specific example of the structure of a compound having the structure shown in FIG. 1;

FIG. 3 illustrates a preparative route to a novel acyclic polyether useful in the formation of rotaxanes and pseudorotaxanes;

FIGS. 4a–b illustrate the structure of a known cyclophane.

Figure 1:
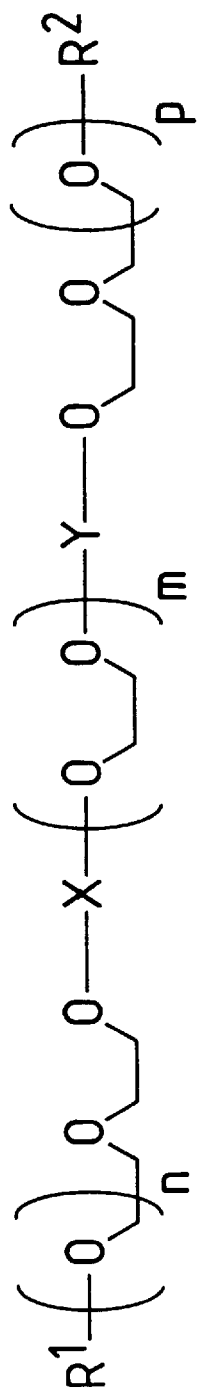
Figure 1:
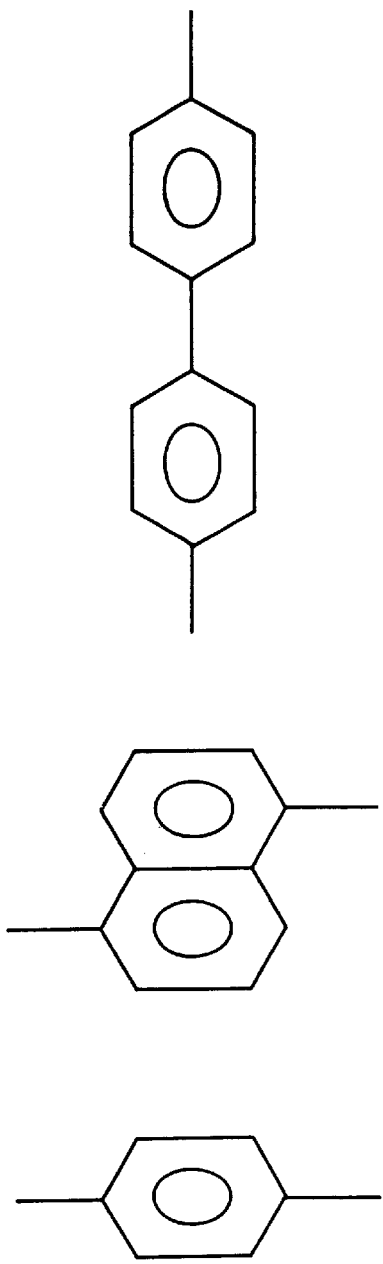
Figure 1:
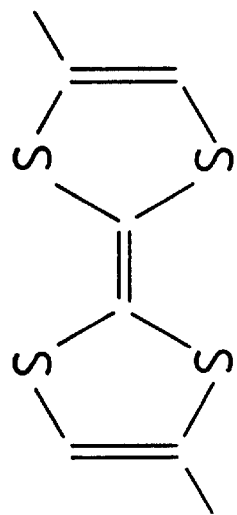

FIG. 1 illustrates a general formula of acyclic polyether compounds suitable for use in the present invention. In FIG. 1, $R^1$ and $R^2$ are neutral terminal units at least one of which includes a cation receptor site; n, m and p are all zero or positive integers and may be the same or different; and x and y each represent a covalent bond or a π-electron-rich functional unit, but where x may or may not be the same as y (and preferably is not) and at least one of x and y is a π-electron-rich functional unit. FIG. 1 also illustrates examples of x and y in a non-limiting sense.

Figure 2A:
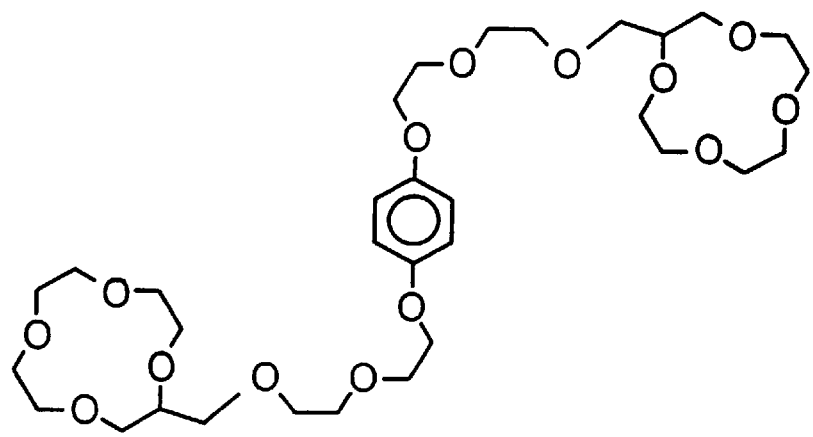
Figure 2B:
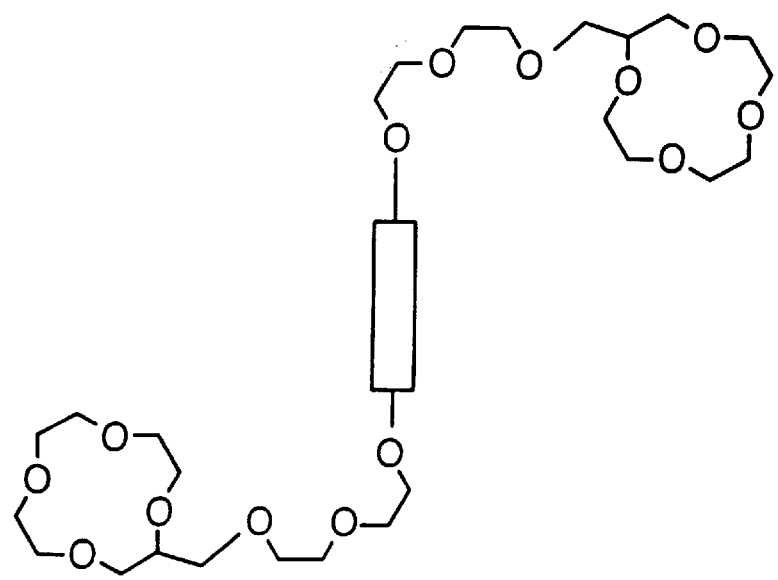

A specific illustrative example of a compound of structure corresponding to component 1 is illustrated in FIG. 2a. The structure is also shown in FIG. 2b by a schematic representation.

Figure 3:
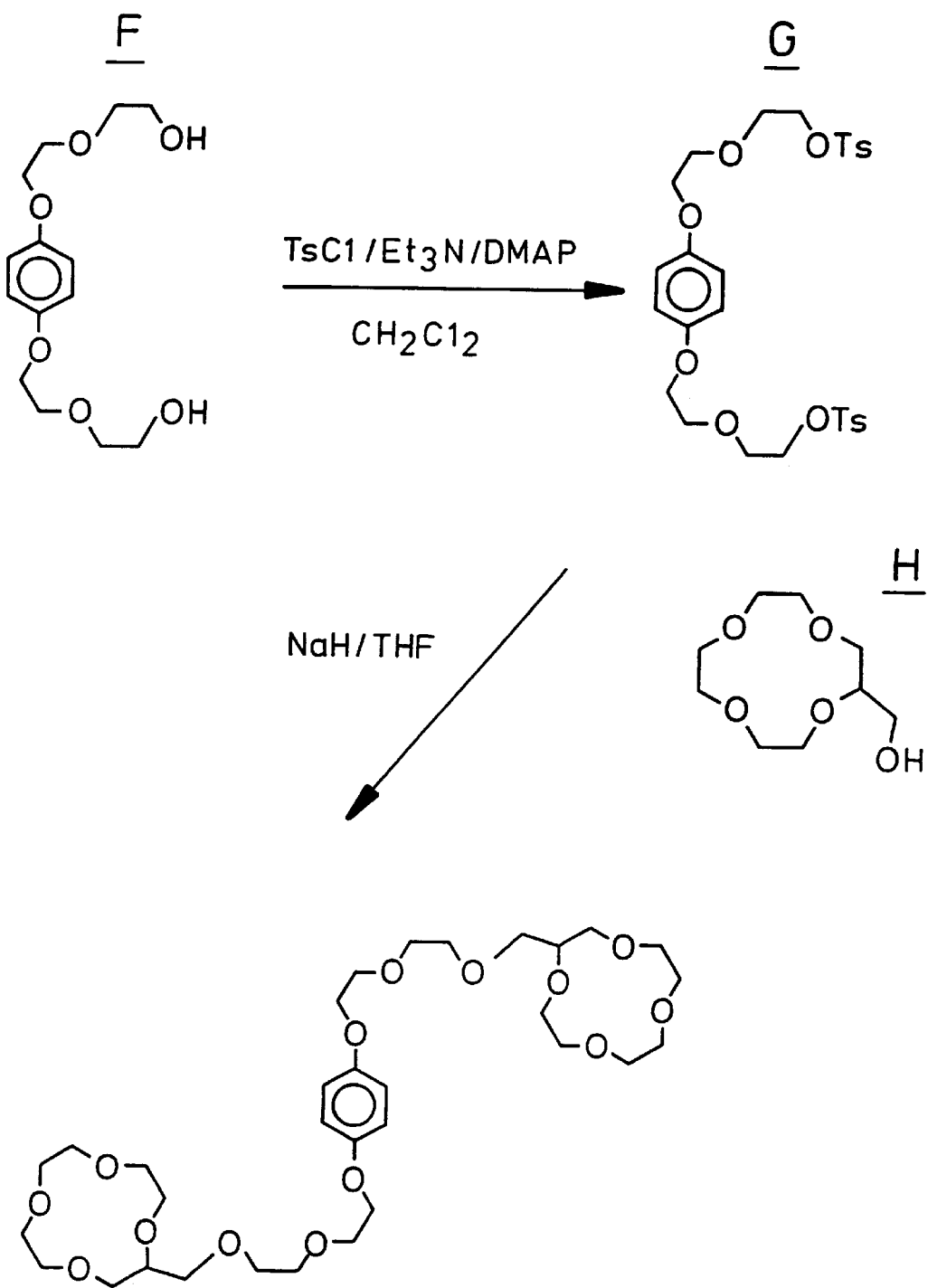

The 1,4-bis(2-(2-(methoxy-12-crown-4)ethoxy)ethoxy) benzene illustrated in FIG. 2 may be prepared as follows and as illustrated in FIG. 3.

This compound may be prepared in two steps from its known corresponding diol, designated as structure F in FIG. 3.

Tosylation of the diol using tosylchloride, triethylamine, 4-dimethylaminopyridine and dichloromethane affords the corresponding bistosylate, designated as structure G in FIG. 3.

Reaction of two equivalents of 2-(hydroxymethyl)-12-crown-4, designated as molecule H in FIG. 3, with the bistosylate in tetrahydrofuran (THF) and in the presence of sodium hydride yields the dumb-bell shaped molecule illustrated in FIG. 2 in 70 per cent yield.

The following data was obtained to characterize the molecule referred to above:

FABMS 662($M^+$)

Figure 4A:
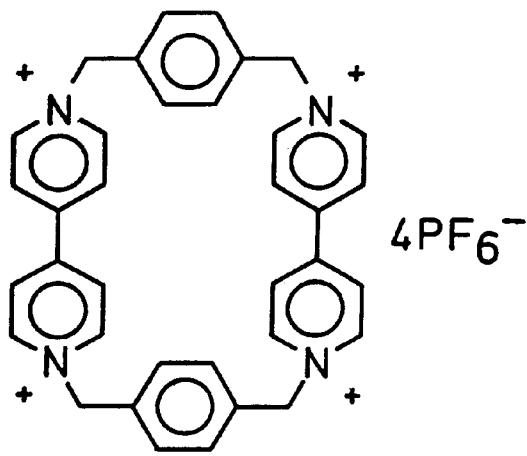
Figure 4B:
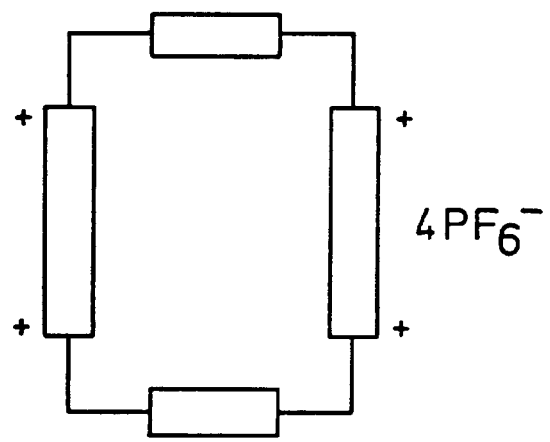

A specific illustrative example of Component 2 is the tetracationic cyclophane shown in FIG. 4a. The structure is also shown in FIG. 4b by a schematic representation.

Rotaxanes and pseudorotaxanes of the present invention are as noted above formed by interaction of Components 1 and 2 as specified above.

Rotaxanes may be made by one of two known assembly mechanisms, viz., (i) a first mechanism in which the cyclophane is clipped around the π-electron rich molecule or (ii) a second mechanism in which an elevated temperature allows the cyclophane to slip over one of the end groups of the π-electron rich molecule. The terminal groups may in principle be added to Component 1 after the rotaxane has been formed but it is likely in practice that the ether chain will be derivatized with terminal groups before it is added to Component 2.

Figure 5:
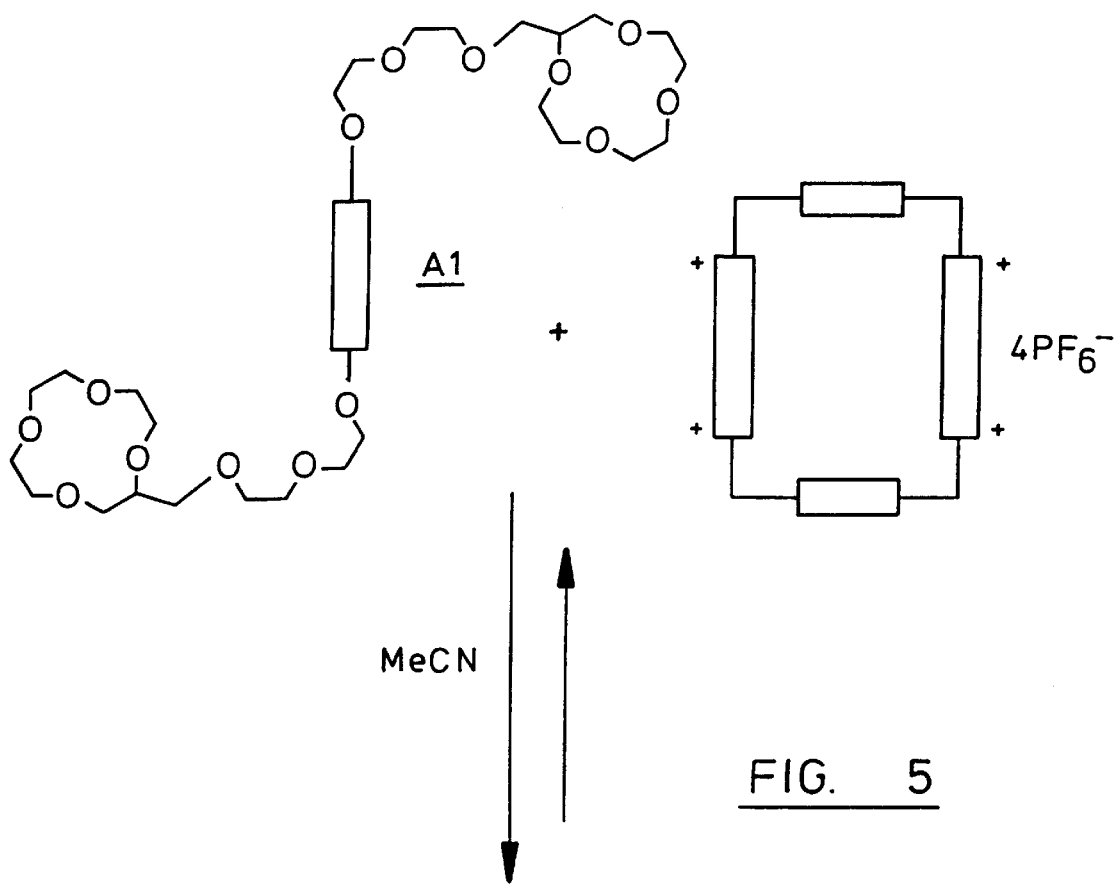
FIG. 5 illustrates formation of a rotaxane/pseudorotaxane embodying the present invention.
Figure 5:
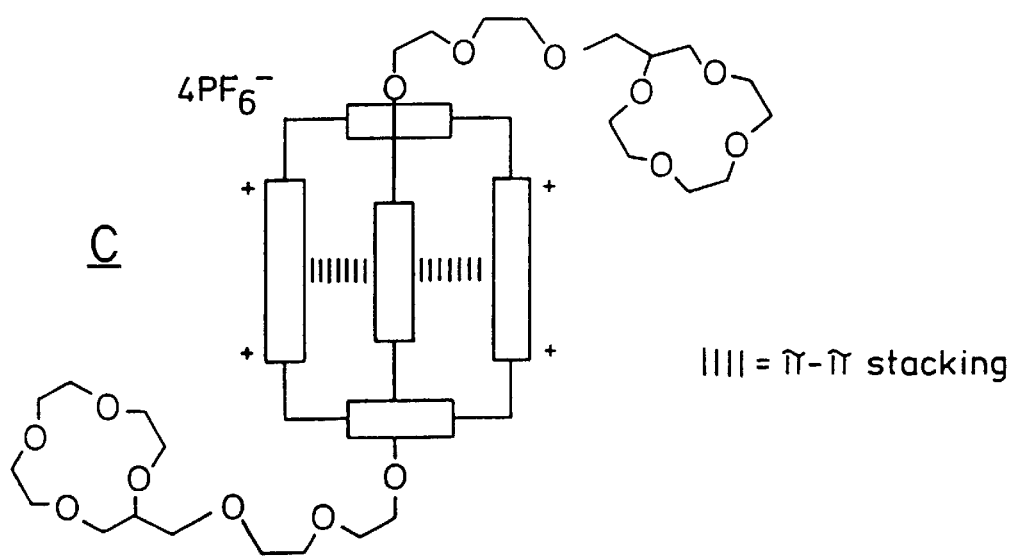

FIG. 5 illustrates an example of formation of rotaxane from Components 1 and 2. Referring to FIG. 5, the acyclic polyether derivative is converted into the multitopic [2]pseudorotaxane, designated in FIG. 5 as molecule of structure C, using the cyclophane as follows. Equimolar solutions of the polyether molecule and the cyclophane both in acetonitrile, are added together at room temperature, 20° C. An intense red/orange colour appears instantaneously on addition of the two components. Combination of Components 1 and 2 in solution in this way leads to a π—π stacked complex by the mechanism of self-assembly in which the cyclophane encircles the acyclic polyether chain.

UV spectroscopic analysis of this solution reveals a charge-transfer between the π electron rich Component 1 and the π electron deficient cyclophane Component 2 which causes absorption of radiation at characteristic wavelengths. Desirably, this provides selective absorption of visible light characteristic of the rotaxane complex. In this example the rotaxane exhibits a strong red/orange coloration; an absorption band in the spectrum at $\lambda_{max}$=466 nm.

A $^1$H NMR spectroscopic titration experiment (25° C., 300 MHz) yielded a binding constant $K_a$. value of 610 dm$^3$ mol$^{-1}$ for the complex. This binding constant is relatively large indicating that in acetonitride solution a [2]pseudorotaxane is the predominant species. As will be noted from the structure shown in FIG. 5 the aromatic unit of the polyether molecule forms a 1:1 inclusive bond in the interior of the cyclophane of structure.

Figure 6:
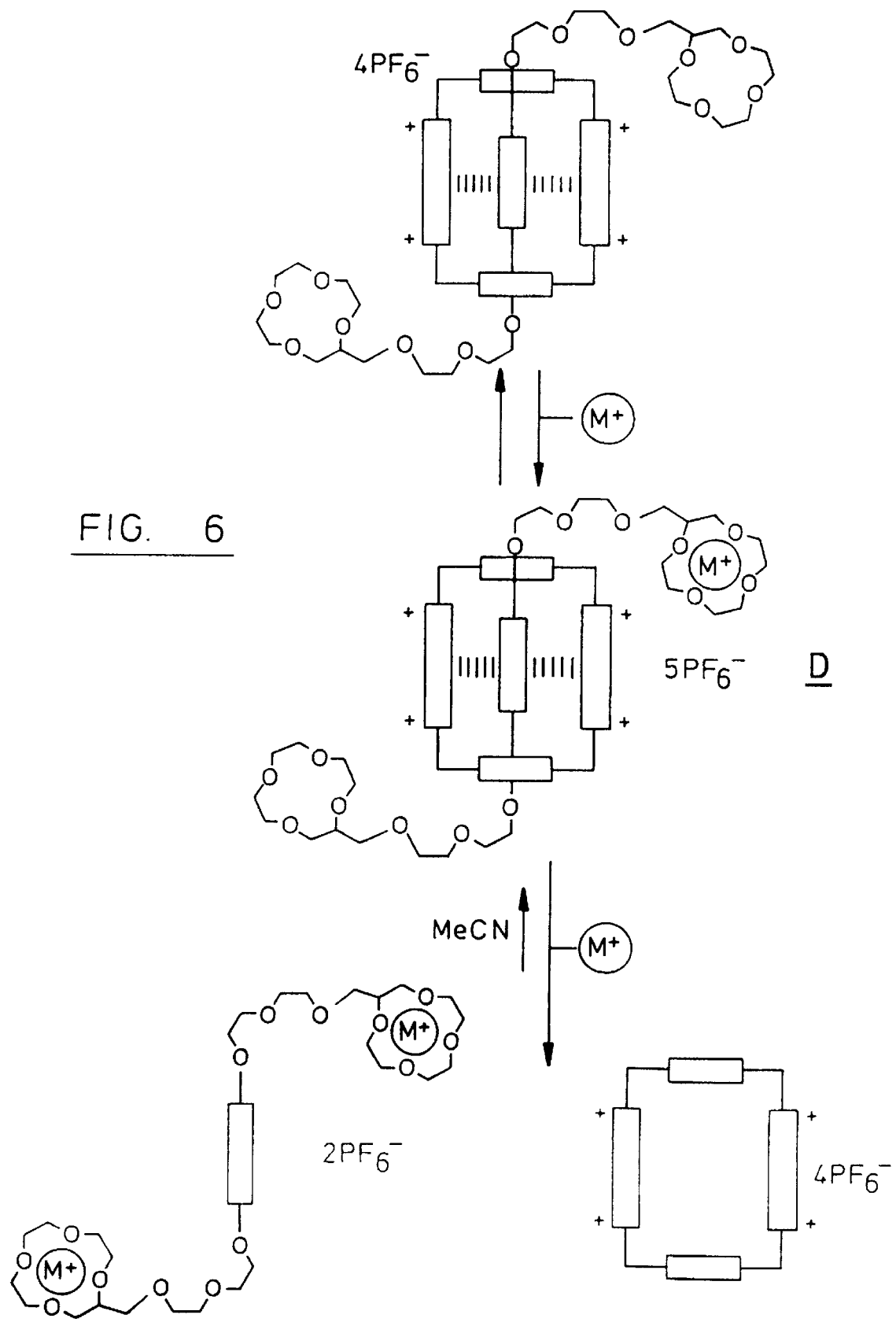
FIG. 6 illustrates metal binding by a rotaxane/pseudorotaxane embodying the present invention.

The mode of action of the rotaxane molecule of FIG. 5 on encountering a metal or other cation is illustrated in FIG. 6. The addition of an excess metal cation, eg Na$^+$, to a solution of the rotaxane leads to a binding of the cation (indicated in FIG. 6 by symbol M$^+$) to a terminal crown ether group to form the unstable metal complex having a structure designated D in FIG. 6. Electrostatic repulsion is produced in the complex between the two cation sites and this results in displacement of the cyclophane unit. Partial, or as illustrated in FIG. 6, total de-threading may occur, in either case the charge transfer is destroyed.

If the polyether chain contains only one electron rich/donor unit, charge transfer is no longer possible and the absorption band and resulting color is diminished. If the polyether chain contains another second, but different, electron rich/donor unit, the cyclophane will be displaced onto this unit preferentially to the ether chain, allowing absorption at a different wavelength, resulting in a colour change. These effects provide the basis of a cation detector since detection of the change or reduction of the charge transfer absorption provides a measure of cation concentration.

In order to quantify the effect, the addition of molar proportions of either $LiPF_6$ or $NaPF_6$ to the [2]pseudorotaxane of structure FIG. 5 in $CD_3CN$ was carried out and led to a gradual suppression of the charge transfer absorption band in the spectrum of the complex of structure D. The addition of a large excess (>10 equivalents) of alkali metal cations brought about almost complete suppression of this absorption band, indicating that the tetracationic cyclophane component was no longer encircling the π-electron rich aromatic portion of component.

Further evidence of dethreading on metal addition was provided by analysis by Liquid Secondary Ion Mass Spectrometry (LSIMS) of the rotaxane complex of FIG. 5. This revealed peaks at m/z 1617, 1472, 1372 corresponding to the loss of one, two and three counterions, respectively. However, the spectrum of the complex following the addition of a solution of $LiPF_6$ or $NaPF_6$ in $CD_3CN$ revealed a dramatic decrease in the intensities of all of those previously observed peaks, indicating again that the [2]pseudorotaxane had dissociated upon addition of a source of metal cations.

As before mentioned where the polyether thread contains another, second, but different donor unit/π-electron-rich unit, the cyclophane will preferentially reside on one of the aromatic donor sites yielding a rotaxane complex absorbing radiation at a characteristic wavelength. However, if a cation is introduced then the electro-static repulsion between the bound cation and the cyclophane unit of the rotaxane causes the cyclophane to dissociate from that π-electron-rich unit. As a result the preferential cyclophane to π-electron-rich unit association is disrupted and the cyclophane instead associates with the alternative π-electron-rich unit. This gives rise to the pseudorotaxane complex absorbing radiation at a different characteristic wavelength.

The aforementioned concept has been demonstrated using a polyether thread containing both 1,4-dioxybenzene and 1,5-dioxynaphthalene donor groups. This polyether thread was synthesised from known precursors in a five step synthesis.

1,4-bis[2-(2-hydroxyethoxy)ethoxy]benzene, F in FIG. 3, was mono-protected using triisopropyl chloride, imidazole and 4-dimethylaminopyridine in dichloromethane. Tosylation of this compound with toluene-p-sulfonyl chloride, 4-dimethylaminopyridine and triethylmane in dichloromethane afforded 1-[2-(2-toluene-p-sulfonyloxy)ethoxy]-4-[2-(2-(triisopropylsilloxy)ethoxy)ethoxy]-benzene.

1,5-bis[2-(2-hydroxyethoxy)ethoxy]naphthalene was mono-protected using dihydropyrane in dichloromethane in the presence of a catalytic amount of pyridinium toluene-p-sulfonate.

Alkylation of this naphthalene derivative with the aforementioned monotosylate using sodium hydride in tetrahydrofuran yielded an unsymmetrical, two donor thread which was subsequently mono-deprotected using pyridinium toluene-p-sulfonate in ethanol to give the required compound.

Addition of cyclophane to an acetonitrile solution of the compound yielded a purple complex which absorbs radiation at 518 nm. This indicates the formation of a pseudorotaxane structure in which the cyclophane resides preferentially on the 1,5-dioxynaphthalene donor group.

Characterisation of the unsymmetrical thread 1H (CDC13, 300 MHz) d 1.06 (21 H, brs, Si(C(CH(CH3) 2)3, 3.65–3.86 (20 H, m, OCH2), 3.98–4.03 (8 H, m, OCH2), 4.28–4.30 (4 H, m, OCH2), 6.81 (4 H, s, HQ), 6.83 (2 H, d, J–8 Hz, NPH2H6), 7.35 (2 H, t, J–8 Hz, NPH3H7), 7.86 (2 H, m, NPH4H8)

13C (CDC13, 75 MHz) d 12.0, 18.0, 61.9, 63.1, 67.9, 68.2, 69.8, 70.0, 70.8, 71.0, 72.6, 72.9, 105.8, 114.5, 114.8, 115.5, 125.0, 125.3, 126.8, 153.1, 154.3.

MS (FAB) M+ 760

As a consequence when the cyclophane unit interacts with a 1,4-dioxybenzene unit the characteristic absorption is λ=466 nm. When the cyclophane unit interacts with the 1,5-dioxynaphthalene unit the characteristic absorption is λ=518 nm. Movement of the cyclophane unit from one unit to another due to repulsion by a cation bound to one of the terminal units affords a measurable change in absorption intensity at the given wavelength—this can be correlated to cation concentration.

With just one π-electron-rich area complete colour loss for a given molecule can give a similarity correlated effect.

As a consequence the detector employing both π-electron-rich groups provides means by which cations concentration can be determined.

What is claimed is:

1. A rotaxane or pseudorotaxane complex which is formed by interaction between an acyclic polyether chain containing at least one π-electron rich unit and an encircling π-electron deficient cyclophane unit, said interaction comprising charge-transfer interaction, said acyclic polyether chain having terminal units that allow for displacement of said polyether chain through said cyclophane unit while inhibiting slippage of the cyclophane unit from the chain, wherein at least one of the terminal units comprises at least one cation-receptor unit, and such that said displacement changes said charge-transfer interaction upon complexation of said at least one cation-receptor unit with a cation.

2. A complex according to claim 1 in which the polyether derivative is of formula:

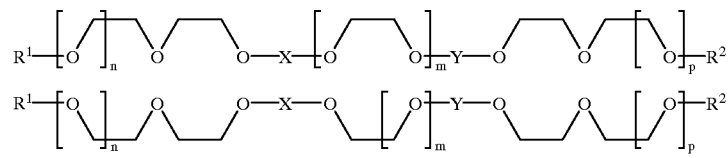

in which $R^1$ and $R^2$ are neutral terminal units at least one of which includes a cation receptor site; n, m and p are independently either zero or a positive integer; x and y each represent a covalent bond or a π-electron-rich functional unit, where x is not the same as y and at least one of x and y is a π-electron-rich functional unit.

3. A complex as in claim 1 and wherein the polyether chain includes one or more π-electron rich aromatic units.

4. A complex as in claim 3 and wherein the polyether chain includes one or more π-electron rich 1,4 dioxybenzene, 1,5 dioxynaphthalene or tetrathiafulvalene groups.

5. A complex as in claim 1 and wherein at least one of the terminal units is selected from crown ethers, azacrown ethers, thiocrown ethers, cyclams, porphyrins, calixanes, calixacrowns and calixaspherands.

6. A complex as in claim 1 and wherein the cyclophane unit comprises an ionic compound.

7. A complex as in claim 6 and wherein the cyclophane is charge balanced by one or more $PF_6^-$ anions.

8. A complex as in claim 1 and which has a cation complexed thereto at the cation receptor site of at least one of its said terminal units.

9. A method of detecting the presence or concentration of cations in a medium which includes bringing a complex as in claim 1 into contact with the medium and detecting changes which occur in the charge transfer absorption spectrum of the complex upon complexation of said at least one cation-receptor unit with a cation.

10. A method as in claim 9 and wherein the complex comprises molecules which are aggregated and supported on a substrate.

11. A method as in claim 9 and wherein the complex is specific to the cations to be detected.

12. An acyclic polyether derivative useful in the formation of a rotaxane as in claim 1 and wherein the polyether chain is a compound having the formula:

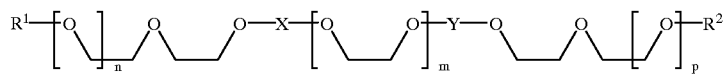

in which $R^1$ and $R^2$ are neutral terminal units at least one of which includes a cation receptor site; n, m and p are independently either zero or a positive integer; x and y each represent a covalent bond or a π-electron-rich functional unit, where x is not the same as y and at least one of x and y is a π-electron-rich functional unit.

13. An acyclic polyether derivative as in claim 12 and wherein the polyether derivative is 1,4-bis(2-2-(methoxy-12-crown-4)ethoxy)ethoxy)benzene or 1,5-bis(2-(2-hydroxyethoxy)ethoxy)naphthalene or incorporates 1,4-dioxybenzene and/or 1,5-dioxynaphthalene.

14. A device for measuring or detecting the presence of a cationic species in a medium comprising a sensor provided with a complex according to claim 1, and means to monitor the charge-transfer light absorption characteristics of the complex upon complexation of said at least one cation-receptor unit with a cation.

15. A rotaxane or pseudorotaxane complex which is formed by interaction between an acyclic polyether chain containing at least one π-electron rich unit and an encircling π-electron deficient cyclophane unit, characterized in that said acyclic polyether chain has terminal units inhibiting slippage of the cyclophane unit from the chain, wherein at least one of the terminal units comprises at least one cation-receptor unit, and said acyclic polyether chain is of either one of formula:

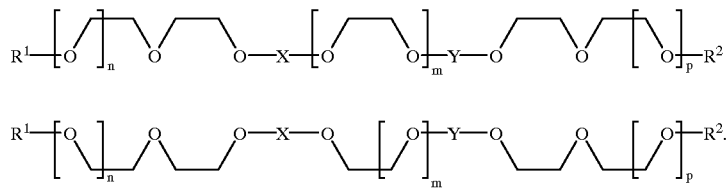

16. An acyclic polyether derivative useful in the formation of a rotaxane or pseudorotaxane complex which is formed by interaction between said acyclic polyether chain containing at least one π-electron rich unit and an encircling π-electron deficient cyclophane unit, and wherein the polyether chain is a compound having the formula:

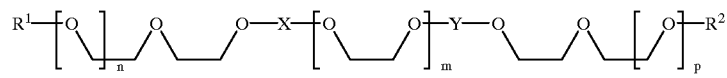

in which $R^1$ and $R^2$ are neutral terminal units at least one of which includes a cation receptor site; n, m and p are independently either zero or a positive integer; x and y each represent a covalent bond or a π-electron-rich functional unit, where x is not the same as y and at least one of x and y is a π-electron-rich functional unit.

17. A rotaxane or pseudorotaxane complex which is formed by interaction between an acyclic polyether chain containing at least one π-electron rich unit and an encircling π-electron deficient cyclophane unit, said interaction comprising charge-transfer interaction, said acyclic polyether chain having terminal units that allow for displacement of said polyether chain such that said displacement leads to the dissociation of said complex, wherein at least one of the terminal units comprises at least one cation-receptor unit, and such that said displacement changes said charge-transfer interaction upon complexation of said at least one cation-receptor unit with a cation.

* * * * *

UNITED STATES PATENT AND TRADEMARK OFFICE
CERTIFICATE OF CORRECTION

PATENT NO. : 6,130,096
DATED : October 10, 2000
INVENTOR(S) : Nigel Dennis Tinker, James Fraser Stoddart, Sayeedha Iqbal, Owen Allen Matthews It is certified that error appears in the above-identified patent and that said Letters Patent is hereby corrected as shown below:

Title page,
Item [30] Foreign Application Priority Data, line 2, change "9511396" to -- 9511396.5 --
Item [56] References Cited, FOREIGN PATENT DOCUMENTS, line 10, change "2 156 144" to -- 2 156 144 B --
Item [56] References Cited, OTHER PUBLICATIONS, after "Templated" change "FFormulation" to -- Formulation --; after "Abstract of" change "conferenced" to -- conference --; after "Patent" change "Application No. JP4265896" to -- Application No. JP 4265896 -- (delete the [n] and insert a space); after "Assemble" change "Lgith" to -- Light --; after "class 3" insert -- , -- (comma); after "Uranium" change "Di Oxide" to -- Dioxide --; after "David J.," change "Moledular" to -- Molecular --; before "Compounds" change "Heterocycllic" to -- Heterocyclic --

Column 1,
Line 8, after "pseudorotaxanes" insert -- , -- (comma)
Line 47, after "integer" insert -- , -- (comma)
Line 48, after "integer;" change X and Y" to -- x and y --
Line 49, after "but where" change "X" to -- x --
Line 50, after "same as" change "Y" to -- y --
Line 50, after "one of" change "X and Y" to -- x and y --
Line 50, after "is" change "an" to -- a --
Line 61, after "thiocrown ethers" insert -- , -- (comma)
Line 64, after "SiPh3" delete [,] (comma)
Line 64, after "arylalkyl" insert -- , -- (comma)
Line 64, after "etc." insert -- ; -- (semicomma)
Line 64, after "phenyl" insert -- , -- (comma)

Column 2,
Line 2, after "24" insert -- , -- (comma)
Line 57, after "toxic" insert -- , -- (comma)
Line 63, after "serum" insert -- , -- (comma)
Line 63, after "etc." insert -- . -- (period)

UNITED STATES PATENT AND TRADEMARK OFFICE
CERTIFICATE OF CORRECTION

PATENT NO.    : 6,130,096
DATED         : October 10, 2000
INVENTOR(S)   : Nigel Dennis Tinker, James Fraser Stoddart, Sayeedha Iqbal, Owen Allen Matthews It is certified that error appears in the above-identified patent and that said Letters Patent is hereby corrected as shown below:

<u>Column 4,</u>
Line 3, before "yield" change "per cent" to -- percent --
Line 21, after "will be" change "derivatized" to -- derived --
Line 30, after "red/orange" change "colour" to -- color --
Line 43, before "value" delete [.] (period)
Line 49, after "cyclophane" delete [of]
Line 52, after "cation," change "eg" to -- e.g., --
Line 58, after "unit." change "Partial, or as" to -- Partial or, as --
Line 66, before "change" change "colour" to -- color --

<u>Column 5,</u>
Line 12, after "portion of" insert -- the --
Line 17, after "one, two" insert -- , -- (comma)
Line 39, after "was" change "synthesised" to -- synthesized --

<u>Column 6,</u>
Line 7, change "Characterisation" to -- Characterization --
Line 7, after "thread" insert -- : -- (colon)
Line 32, after "complete" change "colour" to -- color --
Line 36, before "concentration" change "cations" to -- cation --

Signed and Sealed this

Second Day of April, 2002

*Attest:*

JAMES E. ROGAN
*Director of the United States Patent and Trademark Office*

*Attesting Officer*